United States Patent [19]

Ferland et al.

[11] 4,170,653

[45] Oct. 9, 1979

[54] ANTIDEPRESSANT NAPHTHYLOXY PIPERIDINO AND PYRROLIDINO PROPANOL ETHERS

[75] Inventors: Jean-Marie Ferland, St. Laurent; Real Laliberte, Chomedey; Wilbur Lippmann, Montreal; Thomas A. Pugsley, Kirkland, all of Canada

[73] Assignee: Ayerst McKenna and Harrison Limited, Montreal, Canada

[21] Appl. No.: 829,769

[22] Filed: Sep. 1, 1977

Related U.S. Application Data

[62] Division of Ser. No. 687,851, May 19, 1976, Pat. No. 4,060,613.

[51] Int. Cl.$^2$ .................. A61K 31/445; C07D 211/14
[52] U.S. Cl. ........................... 424/267; 260/326.5 C; 260/326.5 M; 424/274; 544/171; 544/398; 544/399; 544/401; 546/206; 546/236; 546/238; 546/240
[58] Field of Search ...................... 260/293.83, 293.82, 260/326.5 M, 326.5 C, 326.47, 293.62; 424/267, 274; 546/206

[56] References Cited

U.S. PATENT DOCUMENTS

| | | | |
|---|---|---|---|
| 2,738,351 | 3/1956 | Dickison et al. | 546/236 |
| 3,818,000 | 6/1974 | Mauvernay | 260/326.5 M |
| 3,951,978 | 4/1976 | Manghisi | 424/250 X |
| 3,951,983 | 4/1976 | Danilewicz et al. | 546/394 |
| 4,071,552 | 1/1978 | Ferland et al. | 260/293.83 X |

FOREIGN PATENT DOCUMENTS

| | | |
|---|---|---|
| 820938 | 4/1975 | Belgium . |
| 2267104 | 7/1975 | France . |
| 1317034 | 5/1973 | United Kingdom . |
| 1361863 | 7/1974 | United Kingdom . |

OTHER PUBLICATIONS

Beasley, Y. et al., *J. Pharm. & Pharmacol.*, 10, 47–59 (1958).
Black, J. et al., *Lancet*, 1,1080 (1964).
Dauksas, V. et al., *Zh. Vses. Khim. Obshchestva Im. D. I. Mendeleeva*, 9, 352 (1964).
Howe, R., *J. Med. Chem.*, 13, 398 (1970).
*Chemical Abstracts*, 52: 14524e (1958).
*Chemical Abstracts*, 45: 551e (1951).

*Primary Examiner*—John M. Ford
*Assistant Examiner*—Richard A. Schwartz
*Attorney, Agent, or Firm*—Adley F. Mandel

[57] ABSTRACT

Disclosed herein are compounds of the formula

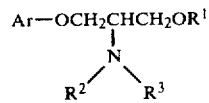

in which Ar is phenyl or 1-naphthyl; $R^1$ is hydrogen or lower alkyl; and $R^2$ and $R^3$ together with the nitrogen atom to which they are joined form a heterocyclic amine radical selected from the group consisting of 1-pyrrolidinyl, piperidino, morpholino and 4-(lower alkyl)-1-piperazinyl. The compounds are antidepressant agents and methods for their preparation and use also are disclosed.

7 Claims, No Drawings

ANTIDEPRESSANT NAPHTHYLOXY PIPERIDINO AND PYRROLIDINO PROPANOL ETHERS

This is a division of application Ser. No. 687,851, filed May 19, 1976, now U.S. Pat. No. 4,060,613, issued Nov. 29, 1977.

BACKGROUND OF THE INVENTION (a) Field of the Invention

This invention relates to aryloxy aminopropanols having antidepressant activity, to a process for their preparation, to intermediates used for the process, and to pharmaceutical compositions and a method of use for these aryloxy aminopropanols.

(b) Prior Art

During the last few decades, psychotherapy has become more effective due to the adjunct use of new central nervous system agents, in particular, the use of tranquilizers and antidepressants. As a consequence the development of new and useful agents for psychotherapy has been diligently pursued, and the finding of a potent, well tolerated agent is noteworthy indeed.

The present invention discloses a group of antidepressant agents having these attributes. The agents are aryloxy aminopropanols. A number of aryloxy aminopropanols are known to possess pharmacologic properties; for example, 1-isopropylamino-3-(1-naphthyloxy)-2-propanol, J. W. Black, et al., Lancet, 1, 1080(1964), a potent $\beta$-blocking agent, and a group of alkyl ethers of 3-amino-1-phenoxy-2-propanol derivatives, V. Dauksas and L. Pikunaite, Zh. Vses. Khim. Obshchestva im. D. I. Mendeleeva, 9, 352 (1964); Chem. Abstr., 61, 6942c(1964) having a stimulating effect on the central nervous system. The compounds of the present invention are distinguished readily from the prior art compounds by having a different structural relationship with respect to the substituents. A compound, 2-isopropylamino-3-(1-naphthyloxy)-1-propanol, having the same structural relationship respecting the substituents has been reported, R. Howe, J. Med. Chem., 13 398 (1970). The compound was devoid of $\beta$-receptor blocking activity in the only pharmacological testing reported therefor. When tested for antidepressant activity according to methods described herein, the compound was found to be devoid of or to have marginal activity.

SUMMARY OF THE INVENTION

The compounds of this invention are represented by formula 1

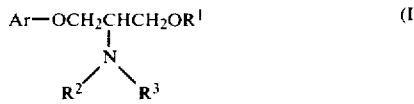

(1)

in which Ar is phenyl or 1-naphthyl; $R^1$ is hydrogen, lower alkyl; and $R^2$ and $R^3$ together with the nitrogen atom to which they are joined form a heterocyclic amine radical selected from the group consisting of 1-pyrrolidinyl, piperidino, morpholino and 4-(lower alkyl)-1-piperazinyl; or a therapeutically acceptable salt thereof.

Pharmaceutical compositions comprising the compound of formula 1, or a therapeutically acceptable acid addition salt thereof, and a pharmaceutically acceptable carrier are included within the scope of this invention.

Also included is a method for alleviating the symptoms of depression in mammals by administering to said animals an effective dose of the compound of formula 1, or a therapeutically acceptable salt thereof.

DETAILS OF THE INVENTION

The term "lower alkyl" as used herein contemplates straight chain alkyl radicals containing from one to six carbon atoms and branched chain alkyl radicals containing three to four carbon atoms and includes methyl, ethyl, propyl, isopropyl, butyl, isobutyl, hexyl and the like.

The term "lower alkanoic acid" as used herein contemplates both straight and branched chain alkanoic acids containing from one to six carbon atoms and includes formic, acetic, propionic, tert-butanoic, pentanoic, hexanoic acids and the like.

The compounds of formula 1 are capable of forming acid addition salts with therapeutically acceptable acids. Such acid addition salts are included within the scope of this invention.

The acid addition salts are prepared by reacting the corresponding base form of the compound of formula 1 with at least one equivalent, or preferably with an excess of the appropriate acid in an organic solvent, for example, ether or an ethanol-ether mixture. These salts, when administered to mammals, possess the same pharmacologic activities as the corresponding bases. For many purposes it is preferable to administer the salts rather than the base compounds. Among the acid addition salts suitable for this purpose are salts such as the sulfate, phosphate, lactate, tartrate, maleate, citrate, hydrobromide and hydrochloride. Both the base compounds and the salts have the distinct advantage of possessing a relatively low order of toxicity.

Also included in this invention are the stereochemical isomers of the compounds of formula 1 which result from asymmetric centers contained therein.

Individual optical isomers, which might be separated by fractional crystallization of the diastereoisomeric salts thereof, for instance, salts with d- or l-tartaric acid or D-(+)-α-bromocamphor sulfonic acid, are also included.

The antidepressant activity of the compounds of formula 1 and their acid addition salts with pharmaceutically acceptable acids is demonstrated in standard pharmacologic tests such as, for example, the tests described by F. Hafliger and V. Burckhart in "Psychopharmacological Agents", M. Gordon, Ed., Academic Press, New York and London, 1964, pp. 75–83.

More specifically, as noted in the latter reference the antidepressant properties of a compound may be demonstrated by its capacity to antagonize the depressant effects of reserpine. Furthermore, it is well documented that reserpine in animals produces a model depression which can be used for detecting antidepressant properties. Accordingly, the compounds of the present invention antagonize reserpine effects in mice at doses ranging from about 1 to 100 mg/kg.

The antidepressant activity of the compounds of formula 1 is also demonstrated by the method of D. F. Bogdanski, et al., J. Pharmacol. Exp. Ther., 122, 182 (1958) which measures the effect of the test compound on the 5-hydroxytryptophan(5-HTP)-induced syndrome. In this test the degree of intensity of the 5-HTP-induced syndrome, i.e. extension and abduction of hindlimbs, lordosis, tremors, head movements and excitation, following the administration of the test compound to Swiss albino mice, is indicated by a scale ranging from +1 (weak effect) to +4 (very strong effect). A positive score in the test is indicative of antidepressant agents having desirable mood elevation properties, see A. Carlsson, et al., Eur. J. Pharmacol., 5, 357 (1969). Several of the preferred compounds, for example, 1-{[1-(ethoxymethyl)-2-(1-naphthyloxy)]ethyl}piperidine hydrochloride, produces a significant effect (+1 to +3) on the 5-HTP-induced syndrome at doses of 6.25 to 25 mg/kg, i.p., when administered to mice (five per group) 30 minutes prior to the 5-HTP injection (300 mg/kg, i.p.).

The following table illustrates further a comparative study of 1-{[1-(ethoxymethyl)-2-(1-naphthyloxy)]ethyl}piperidine hydrochloride, imipramine hydrochloride and desimipramine hydrochloride in the potentiation of the 5-HTP-syndrome test.

| Compound | Dose(mg/kg,i.p.) | Behavioral Score |
|---|---|---|
| saline | — | 0 |
| 1-{[1-(ethoxymethyl)-2-(1-naphthyloxy)]ethyl}-piperidine hydrochloride (Example 4) | 25 | +3 |
|  | 12.5 | +1 |
|  | 6.25 | +1 |
| imipramine hydrochloride | 25 | +3 |
|  | 12.5 | +2 |
|  | 6.25 | +1 |
| desimipramine hydrochloride | 25 | +1 |

When the compounds of formula 1 were used as antidepressants in mammals, e.g. rats and mice, they may be used alone or in combination with pharmacologically acceptable carriers, the proportion of which is determined by the solubility and chemical nature of the compound, chosen route of administration and standard biological practice. For example, they are administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present invention therapeutic agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 100 mg/kg per day, although as aforementioned variations will occur. However, a dosage level that is in the range of from about 0.5 mg to about 50 mg/kg per day is most desirably employed in order to achieve effective results.

The compounds of formula 1 in which $R^1$ is hydrogen an Ar, $R^2$ and $R^3$ are as defined herein are prepared by a process represented by the following flow diagram.

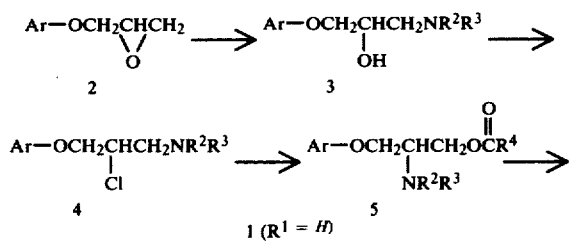

The starting material of formula 2 in which Ar is phenyl, 1,2-epoxy-3-phenoxy-propane, is described by W. Bradley, J. Forrest and O. Stephenson, J. Chem. Soc., 1589 (1959) and the starting material of formula 2 in which Ar is 1-naphthyl, 1,2-epoxy-3-(1-naphthoxy)-propane, is described by A. F. Crowther and L. H. Smith, J. Med. Chem., 11, 1009 (1968).

With reference to the flow diagram, the compounds of formula 1 in which $R^1$ is hydrogen and Ar, $R^2$ and $R^3$ are as defined herein are prepared by a process comprising: reacting the starting material of formula 2 with an amine of formula $NHR^2R^3$ in which $R^2$ and $R^3$ are as defined herein to obtain the $\beta$-hydroxypropylamine of formula 3 in which Ar, $R^2$ and $R^3$ are as defined herein; reacting the last-named compound with p-toluenesulfonic acid chloride or thionyl chloride to obtain the corresponding $\beta$-chloropropylamine of formula 4, reacting the latter compound with a lower alkanoic acid of formula $R^4COOH$ in which $R^4$ is hydrogen or lower alkyl in the presence of an alkali salt of the lower alkanoic acid to obtain the compound of formula 5 in which Ar, $R^2$, $R^3$ and $R^4$ are as defined herein, and hydrolyzing the latter compound with an acid or a base to obtain the corresponding compound of formula 1 in which $R^1$ is hydrogen.

More specifically, convenient conditions for converting the starting material of formula 2 to the hydroxypropylamine of formula 3 include reacting the starting material of formula 2 with about one molar equivalent of the appropriate amine of formula $NHR^2R^3$ in an inert solvent, for example, diethyl ether, methanol or tetrahydrofuran, at 0° to 40° C. for ten minutes to four hours.

Subsequent transformation of the hydroxypropylamine of formula 3 to the corresponding $\beta$-chloropropylamine is conveniently effected by reacting in an inert organic solvent the hydroxypropylamine with about one molar equivalent of tosyl chloride or thionyl chloride, tosyl chloride being preferred, at 10° to 80° C. for two to 24 hours. The reaction is preferably carried out in the presence of an excess of an organic base, for example, triethylamine or pyridine. Suitable inert organic solvents include benzene, diethyl ether or tetrahydrofuran.

Thereafter the $\beta$-chloropropylamine of formula 4 is converted to the compound of formula 5 under mildly acidic condition using an excess of a lower alkanoic acid, preferably acetic acid, in the presence of one to ten molar equivalents of an alkali salt of the lower alkanoic acid, preferably sodium or potassium acetate. It has been found convenient to use the lower alkanoic acid as a solvent for this reaction, and temperatures and times ranging from 10° to 100° C. and one to six hours, respectively. It should be noted that this reaction involves a rearrangement of the amino radical ($NR^2R^3$).

Subsequent hydrolysis of the compound of formula 5 to the corresponding compound of formula 1 in which $R^1$ is hydrogen is effected using an acid or a base as the hydrolysis agent. Hydrolysis is preferably effected with a base. For the basic hydrolysis a preferred embodiment involves subjecting the compound of formula 5 to the action of a strong base, for example, sodium or potassium hydroxide, in the presence of sufficient water to effect hydrolysis. The hydrolysis is performed using a suitable solvent, for example, methanol or ethanol and the reaction mixture is maintained at a temperature of from 25° C. to the reflux temperature until hydrolysis occurs. Usually from ten minutes to six hours is sufficient for this hydrolysis. The reaction mixture is extracted with an organic solvent, for example diethyl ether, and the extract worked up in the usual manner to afford the compound of formula 1 in which $R^1$ is hydrogen.

The compounds of formula 1 in which $R^1$ is lower alkyl and Ar, $R^2$ and $R^3$ are as defined herein are prepared by reacting the above-mentioned β-chloropropylamine of formula 4 with an appropriate alcohol of formula $R^5OH$ in which $R^5$ is lower alkyl in the presence of sodium or potassium alkoxide in which the alkyl portion thereof corresponds to the lower alkyl of $R^5$, preferably one to ten moles. This reaction proceeds readily within about 15 minutes to two hours at 20° to 80° C. using an excess of the alcohol as a reaction medium. When benzyl alcohol is used as the alcohol together with sodium or potassium phenylmethoxide in this reaction, the corresponding benzyl ether is obtained.

The following examples illustrate further this invention.

EXAMPLE 1

3-(1-Pyrrolidinyl)-1-(1-naphthyloxy)-2-propanol (3; Ar=1-naphthyl and $NR^2R^3$=1-pyrrolidinyl)

A solution of 1,2-epoxy-3-(1-naphthyloxy)propane (62.0 g) and the amine of formula $NHR^2R^3$, pyrrolidine (23.5 g), in methanol (250 ml) is heated at reflux for two hours. The reaction mixture is concentrated to dryness. The oily residue is crystallized from chloroform and diethyl ether by the addition of hexane to give the title compound, mp 68°–70° C.

In the same manner but replacing pyrrolidine with an equivalent amount of piperidine, morpholine or N-methylpiperazine,
3-piperidino-1-(1-naphthyloxy)-2-propanol, $\gamma_{max}^{nujol}$3250 and 2655 cm$^{-1}$, (the corresponding hydrochloride of the latter compound has mp 189°–190° C.)
3-morpholino-1-(1-naphthyloxy)-2-propanol, mp 68°–70° C., and
3-(4-methyl-1-piperazinyl)-1-(1-naphthyloxy)-2-propanol, mp 73°–74° C.

In the same manner but replacing 1,2-epoxy-3-(1-naphthyloxy)propane with an equivalent amount of 1,2-epoxy-3-phenoxy-propane and using pyrrolidine, piperidine, morpholine, or 1-methylpiperidine as the amine of formula $NHR^2R^3$,
3-(1-pyrrolidinyl)-1-phenoxy-2-propanol,
3-piperidino-1-phenoxy-2-propanol, mp 52°–54° C.,
3-morpholino-1-phenoxy-2-propanol, and
3-(4-methyl-1-piperazinyl)-1-phenoxy-2-propanol, are obtained, respectively.

EXAMPLE 2

1-{[2-Chloro-3-(1-naphthyloxy)]propyl}pyrrolidine (4; Ar=1-naphthyl and $NR^2R^3$=1-pyrrolidinyl)

A solution of 3-(1-pyrrolidinyl)-1-(1-naphthyloxy)-2-propanol (56 g), described in Example 1, and tosyl chloride (43 g) in benzene (500 ml) is heated at reflux for 18 hours. The mixture is cooled, washed with dilute sodium bicarbonate and extracted with dilute hydrochloric acid. The dilute hydrochloric acid extract is washed with ether, rendered neutral with dilute sodium hydroxide and extracted with chloroform ($CHCl_3$). The $CHCl_3$ extract is dried and concentrated. The residue is subjected to chromatography using silica gel as the absorbent. Elution with diethyl ether-methanol (9:1) yields unchanged starting material. Subsequent elution with diethyl ether-methanol (7:3) yields the title compound.

In the same manner but replacing 3-(1-pyrrolidinyl)-1-(1-naphthyloxy)-2-propanol with an equivalent amount of
3-piperidino-1-(1-naphthyloxy)-2-propanol,
3-morpholino-1-(1-naphthyloxy)-2-propanol,
3-(4-methyl-1-piperazinyl)-1-(1-naphthyloxy)-2-propanol,
3-(1-pyrrolidinyl)-1-phenoxy-2-propanol,
3-piperidino-1-phenoxy-2-propanol,
3-morpholino-1-phenoxy-2-propanol,
3-(1-piperazinyl)-1-phenoxy-2-propanol,
3-(4-methyl-1-piperazinyl)-1-phenoxy-2-propanol, the following β-chloropropylamines of formula 4,
1-{[2-chloro-3-(1-naphthyloxyl)]propyl}piperidine, mp 45°–48° C.,
1-{[2-chloro-3-(1-naphthyloxy)]propyl}morpholine, bp 158°–160° C./0.02 mm/Hg,
1-{[2-chloro-3-(1-naphthyloxy)]propyl}-4-methylpiperazine,
1-[(2-chloro-3-penoxy)propyl]pyrrolidine,
1-[(2-chloro-3-phenoxy)propyl]piperidine (reported by Dauksas and Pikunaite, cited above),
1-[(2-chloro-3-phenoxy)propyl]morpholine,
1-[(2-chloro-3-phenoxy)propyl]piperazine, and
1-[(2-chloro-3-phenoxy)propyl]-4-methylpiperazine, are obtained, respectively.

EXAMPLE 3

2-Piperidino-3-(1-naphthyloxy)-1-propanol (1; Ar=1-naphthyl, $R^1$=H and $NR^2R^3$=piperidino)

A mixture of the compound of formula 4, 1-{[2-chloro-3-(1-naphthyloxy)]propyl}piperidine (10.0 g), described in Example 2, and sodium acetate (5.4 g) in acetic acid (50 g) is heated at reflux for two hours. The mixture is cooled and ether added to the mixture. The resulting solid is collected on a filter. The filtrate is concentrated to dryness. The residue is dissolved in diethyl ether. The solution is washed with dilute $NaHCO_3$, dried and poured onto a column of silica gel. Elution with ethyl acetate-benzene (1:4) gives 2-piperidino-3-(1-naphthyloxy)-2-propanol acetate (5; Ar=1-naphthyl, $NR^2R^3$=piperidino and $R^4$=$CH_3$), $\gamma_{max}^{EtOH}$ 318 nm (ε=1640), 304 nm (ε=3130), 287 nm (ε=6360), 229 nm (ε=29,700), 213 nm (ε=42,900). (Continued elution with ethyl acetate-benzene (1:4) gives the positional isomer, 1-piperidino-3-(1-naphthyloxy)-2-propanol acetate). The hydrochloric acid addition salt of 2-piperidino-3-(1-naphthyloxy)-1-propanol acetate has mp 151°–157° C.

The 2-piperidino-3-(1-naphthyloxy)-1-propanol acetate so obtained is hydrolyzed in the following manner:

A suspension of 2-piperidino-3-(1-naphthyloxy)-1-propanol acetate (6.4 g), 15% KOH in methanol (10 ml), methanol (10 ml) and water (20 ml) is heated at reflux for one hour. The reaction mixture is concentrated to dryness. The residue is taken up in diethyl ether. The ether extract is washed with water and concentrated to give the title compound as an oil, $\gamma_{max}^{EtOH}$ 319 nm ($\epsilon = 1780$), 350 nm ($\epsilon = 3330$), 288 nm ($\epsilon = 6340$), 230 nm ($\epsilon = 30,600$), 212 nm ($\epsilon = 44,180$).

The hydrochloric acid addition salt (hydrochloride) of the title compound has mp 165°–170° C., after recrystallization from methanol-diethyl ether.

In the same manner but replacing 1-{[2-chloro-3-(1-naphthyloxy)]propyl}piperidine with another compound of formula 4, described in Example 2, other corresponding compounds of formula 1 in which $R^1$ is hydrogen are obtained. For instance, replacement with
1-{[2-chloro-3-(1-naphthyloxy)]propyl}pyrrolidine,
1-{[2-chloro-3-(1-naphthyloxy)]propyl}morpholine,
1-{[2-chloro-3-(1-naphthyloxy)]propyl}-4-methylpiperazine,
1-[(2-chloro-3-phenoxy)propyl]pyrrolidine,
1-[(2-chloro-3-phenoxy)propyl]piperidine,
1-[(2-chloro-3-phenoxy)propyl]morpholine, or
1-[(2-chloro-3-phenoxy)propyl]-4-methylpiperzine, gives
2-(1-pyrrolidinyl)-3-(1-naphthyloxy)-1-propanol,
2-morpholino-3-(1-naphthyloxy)-1-propanol,
2-(4-methyl-1-piperazinyl)-3-(1-naphthyloxy)-1-propanol,
2-(1-pyrrolidinyl)-3-phenoxy-1-propanol,
2-piperazino-3-phenoxy-1-propanol,
2-morpholino-3-phenoxy-1-propanol, and
2-(4-methyl-1-piperazinyl)-3-phenoxy-1-propanol, respectively.

EXAMPLE 4

1-{[1-(Ethoxymethyl)-2-(1-naphthyloxy)]ethyl}piperidine (1; Ar = 1-naphthyl, $R^1 = C_2H_5$ and $NR^2R^3$ = piperidino)

The compound of formula 4, 1-{[2-chloro-3-(1-naphthyloxy)]propyl}piperidine (7.0 g), is added to a solution of sodium (0.54 g) in ethanol (70 ml), i.e. the alcohol of formula $R^5OH$ in which $R^5$ is ethyl. The mixture is heated at reflux for one hour and cooled. Precipitated sodium chloride is collected on a filter and the filtrate is evaporated to yield an oil. The oil is subjected to chromatography on silica gel. Elution with diethyl ether-hexane (1:1) gives the title compound, $\gamma_{max}^{EtOH}$ 319 nm ($\epsilon = 1710$), 304 nm ($\epsilon = 3290$), 289 nm ($\epsilon = 6400$), 223 nm ($\epsilon = 31,100$), 212 nm ($\epsilon = 44,300$).

The corresponding hydrochloric acid addition salt of the title compound has mp 151°–156° C., after recrystallization from methanol-diethyl ether.

In the same manner but replacing 1-{[2-chloro-3-(1-naphthyloxy)]propyl}piperidine with another compound of formula 4, described in Example 2 and using the appropriate alcohol of formula $R^5OH$, other corresponding compounds of formula 1 in which $R^1$ is lower alkyl is obtained. For instance, replacement with
1-{[2-chloro-3-(1-naphthyloxy)]propyl}pyrrolidine,
1-{[2-chloro-3-(1-naphthyloxy)]propyl}morpholine,
1-{[2-chloro-3-(1-naphthyloxy)]propyl}-4-methylpiperazine,
1-[(2-chloro-3-phenoxy)propyl]pyrrolidine,
1-[(2-chloro-3-phenoxy)propyl]piperidine,
1-[(2-chloro-3-phenoxy)propyl]morpholine, or
1-[(2-chloro-3-phenoxy)propyl]-4-methylpiperazine,
and using ethanol as the alcohol of formula $R^5OH$, gives
1-{[1-(ethoxymethyl)-2-(1-naphthyloxy)]ethyl}pyrrolidine, $\gamma_{max}^{CHCl_3}$ 1595, 1580, 1460, 1245 and 1270 cm$^{-1}$, the corresponding hydrochloric acid addition salt of the latter compound has mp 168°–170° C.,
1-{[1-(ethoxymethyl)-2-(1-naphthyloxy)]ethyl}morpholine,
1-{[1-(ethoxymethyl)-2-(1-naphthyloxy)]ethyl}-4-methylpiperazine, $\gamma_{max}^{CHCl_3}$ 1595, 1580, 1460, 1238 and 1270 cm$^{-1}$, the corresponding hydrochloric acid addition salt (dihydrochloride) of the latter compound has mp 160°–165° C.
1-{[1-(ethoxymethyl)-2-phenoxy]ethyl}pyrrolidine,
1-{[1-(ethoxymethyl)-2-phenoxy]ethyl}piperidine, $\gamma_{max}^{CHCl_3}$ 1595, 1577, 1450 and 1220 cm$^{-1}$, the corresponding hydrochloric acid addition salt of the latter compound has mp 85°–90° C.,
1-{[1-(ethoxymethyl)-2-phenoxy]ethyl}morpholine, or
1-{[1-(ethoxymethyl)-2-phenoxy]ethyl}-4-methylpiperazine, respectively.

Furthermore, in the same manner and using the appropriate compound of formula 4 and benzyl alcohol as the alcohol, corresponding benzyl ethers are obtained. For example, 1-{[2-chloro-3-(1-naphthyloxy)]propyl}piperidine and benzyl alcohol gives 1-{[2-(1-naphthyloxy)-1-(phenylmethoxymethyl)]ethyl}piperidine, the hydrochloric acid addition salt of the latter compound has mp 145°–148° C., after recrystallization from methanol and ether.

1-{[2-chloro-3-(1-naphthyloxy)]propyl}morpholine and benzyl alcohol give 1-{[2-(1-naphthloxy)-1-(phenylmethoxymethyl)]ethyl}morpholine, the hydrochloric acid addition salt of the latter compound has mp 130°–145° C., after recrystallization from methanol and ether.

1-[(2-chloro-3-phenoxy)propyl]piperidine and benzyl alcohol give 1-{[2-phenoxy-1-(phenylmethoxymethyl)]ethyl}piperidine, the hydrochloric acid addition salt of the latter compound has mp 86°–93° C., after recrystallization from isopropanol and diethyl ether.

We claim:
1. A compound of the formula 1

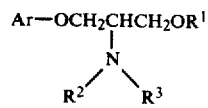

in which Ar is 1-naphthyl, $R^1$ is lower alkyl containing from one to six carbon atoms in a straight chain and three to four carbon atoms in a branched chain; and $R^2$ and $R^3$ together with the nitrogen atom to which they are joined from a heterocyclic amine radical selected from the group consisting of 1-pyrrolidinyl and piperidino; or a therapeutically acceptable acid addition salt thereof.

2. 1-{[1-(Ethoxymethyl)-2-(1-naphthyloxy)]ethyl}-piperidine, as claimed in claim 1.

3. 1-{[1-(Ethoxymethyl)-2-(1-naphthyloxy)]ethyl}-piperidine hydrochloride, as claimed in claim 1.

4. 1-{[1-(Ethoxymethyl)-2-(1-naphthyloxy)]ethyl}-pyrrolidine, as claimed in claim 1.

5. 1-{[1-(Ethoxymethyl)-2-(1-naphthyloxy)]ethyl}-pyrrolidine hydrochloride, as claimed in claim 1.

6. A pharmaceutical composition having antidepressant activity comprising a compound of formula 1 of claim 1, or a therapeutically acceptable acid addition salt thereof at a dosage from about 0.1 mg. to about 100 mg/kg per day, and a pharmaceutically acceptable carrier.

7. A method of alleviating symptoms of depression in a mammal comprising administering to said mammal an effective dose from about 0.1 mg. to about 100 mg. per kilogram per day of a compound of formula 1 to claim 1, or a therapeutically acceptable acid addition salt thereof.

* * * * *